(12) United States Patent
Rodriguez et al.

(10) Patent No.: US 11,033,724 B2
(45) Date of Patent: Jun. 15, 2021

(54) TATTOOING APPARATUS

(71) Applicant: Hand of Glory Tattoo Studio Inc., Walton, NY (US)

(72) Inventors: Craig J. Rodriguez, Walton, NY (US); Cain R. Rodriguez, Walton, NY (US)

(73) Assignee: Hand of Glory Tattoo Studio Inc., Walton, NY (US)

( * ) Notice: Subject to any disclaimer, the term of this patent is extended or adjusted under 35 U.S.C. 154(b) by 214 days.

(21) Appl. No.: 16/231,482

(22) Filed: Dec. 22, 2018

(65) Prior Publication Data

US 2020/0197680 A1    Jun. 25, 2020

(51) Int. Cl.
A61M 37/00    (2006.01)

(52) U.S. Cl.
CPC ............... A61M 37/0076 (2013.01)

(58) Field of Classification Search
CPC .............. A61M 37/0076; A61M 37/00; A61M 37/0084; A01K 11/005
See application file for complete search history.

(56) References Cited

U.S. PATENT DOCUMENTS

| | | | | |
|---|---|---|---|---|
| 10,835,725 B2* | 11/2020 | Xiao | ................. | A61M 37/0084 |
| 2008/0055028 A1* | 3/2008 | Mask | ..................... | H02K 33/16 335/229 |
| 2012/0192681 A1* | 8/2012 | Klebs | ................ | A61M 37/0076 81/9.22 |
| 2012/0265232 A1* | 10/2012 | Surbone | ............ | A61M 37/0076 606/186 |
| 2016/0074645 A1* | 3/2016 | Siciliano | ........... | A61M 37/0076 81/9.22 |
| 2018/0056055 A1* | 3/2018 | Rutherford | ....... | A61M 37/0076 |

OTHER PUBLICATIONS

12 Triple Stacked Magnum-Precision Needles, https://www.painfulpleasures.com/tattoo-supplies/tattoo-needles/precision-tattoo-needles/12-triple-stacked-magnum-premade-sterilized-tattoo-needles-on-bar-box-of-50.html.

* cited by examiner

Primary Examiner — George J Ulsh
(74) Attorney, Agent, or Firm — Brown & Michaels, PC

(57) ABSTRACT

A tattooing apparatus includes a grip body and a pivot pin. The grip body defines a cavity extending entirely through the grip body in a first direction. The pivot pin is mounted in the cavity perpendicular to the first direction, the pivot pin having an axis of rotation, the pivot pin mounted rotatably around the axis of rotation.

A tattoo needle assembly includes a needle bar, a loop, and a plurality of needles. The needle bar has a first end and a second end. The loop is coupled to the first end and defines a first plane. The plurality of needles includes a first row coupled to the second end and defining a second plane, the first plane angled approximately 90 degrees to the second plane.

A tattoo needle assembly includes three rows of at least three needles, the needles fastened together to be immovable with respect to each other.

13 Claims, 8 Drawing Sheets

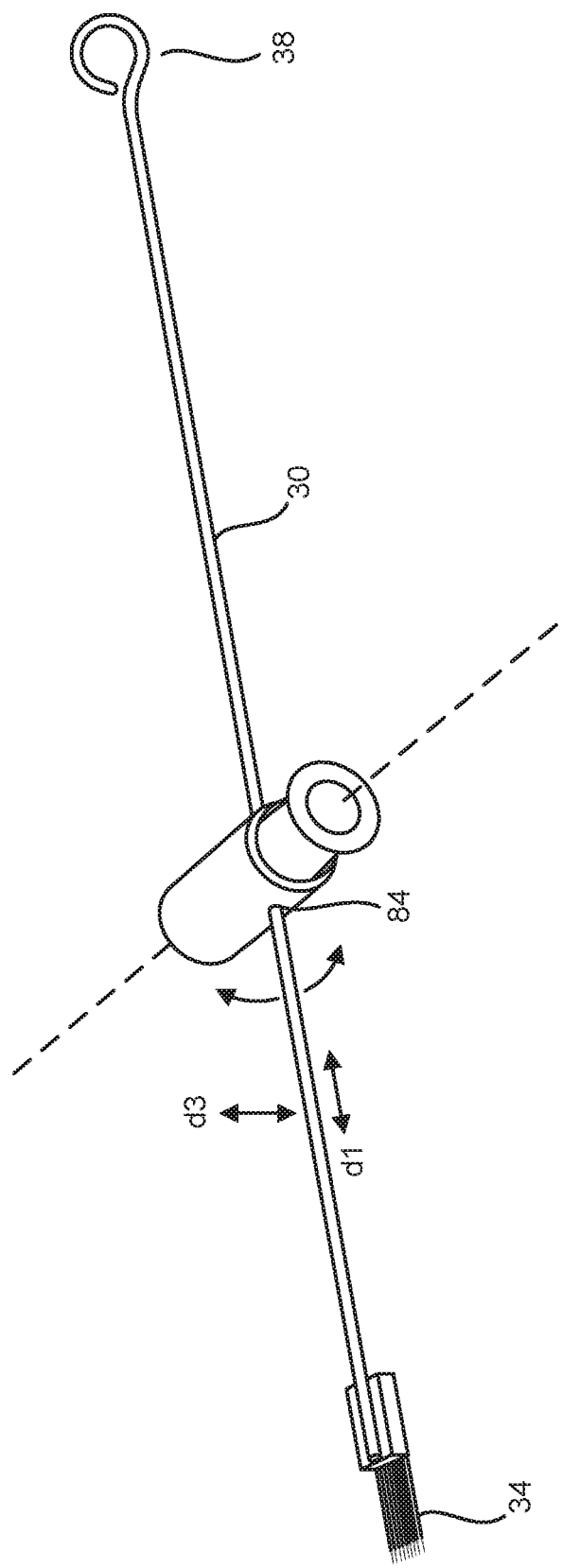

TATTOOING APPARATUS

FIELD OF THE INVENTION

The present invention relates to a tattooing apparatus and, more specifically, to a needle bar, needle group, grip body, and grip assembly of a tattooing apparatus.

BACKGROUND OF THE INVENTION

A tattooing apparatus, sometimes called a tattoo machine or a tattoo machine with grip and needle system, is a hand-held device used to create a tattoo, which is a permanent marking of the skin with indelible ink. Conventional tattoo apparatuses use electromagnetic coils, regulated motors, or other motion-powering devices to reciprocate a group of needles attached to an end of a needle bar. The needles reciprocate linearly, and in many cases, within a tubular or cylindrical structure from which the needles retrieve ink each cycle to carry into skin of an individual being tattooed. The reciprocating needles repeatedly puncture the skin and inject the ink into the dermis or second layer of the skin just below the epidermis.

FIG. 1 shows an embodiment of a conventional rotary tattooing apparatus 1. A needle bar 2 extends from a group of needles 3 through a grip body 4 to a loop 5. The loop 5 couples with a driver element 6, which is offset radially from a rotational axis 7 of a cam 8. The cam 8 can be rotated around the rotational axis 7, which drives the driver element 6 and the loop 5 circularly around the rotational axis 7 of the offset cam 8. The circularly reciprocating motion of the driver element 6 and the loop 5 translates into a linear motion of the needles 3 in the piercing and retracting directions d1 because "side" retaining walls 9 surrounding the needles 3 restrict the components of motion in the directions d2, which are orthogonal to the piercing and retracting directions.

The longevity or "permanency" of a tattoo owes primarily to the relatively large size of pigment particles in tattoo ink. The body responds to the introduction of foreign material by sending white blood cells (e.g., macrophages) to the tattooed skin area in an attempt to absorb the foreign pigment particles and dispose of them in the blood stream. The tattoo pigment particles are too big to be eaten by the white cells, though, so the tattoo ink pigment particles remain.

Even permanent tattoos can fade over time, though. Changes in the skin can break larger particles into smaller particles, and electromagnetic radiation piercing the skin can cause decomposition of the tattoo pigment particles, for example. Smaller particles are unable to endure as much physical damage as larger particles before being small enough for the body to remove the particles. Further, because of their larger total surface area, smaller particles are more prone to decomposition initiated by chemical agents or light. As particles break or decompose, fading results, which can decrease the vibrancy and quality of a tattoo over time.

SUMMARY OF THE INVENTION

A tattooing apparatus, a grip body, a tattoo needle bar, and a pivot pin for a tattooing apparatus are disclosed. The embodiments described herein facilitate non-linearly reciprocating motion of the needle bar to widen skin piercings for deposition of larger and/or greater quantities of ink pigment particles. The larger ink pigment particles yield tattoos with greater longevity in color vibrancy.

In an embodiment, a tattooing apparatus includes: a grip body defining a cavity extending entirely through the grip body in a first direction; and a pivot pin mounted in the cavity perpendicular to the first direction, the pivot pin having an axis of rotation, the pivot pin being mounted rotatably around the axis of rotation.

In another embodiment, a tattoo needle assembly includes: a needle bar having a first end and a second end; a loop coupled to the first end, the loop defining a first plane; and a plurality of needles, the plurality of needles including a first row coupled to the second end and defining a second plane, the first plane angled approximately 90 degrees relative to the second plane.

In another embodiment, a tattoo needle assembly includes three rows of needles, at least three needles in each row, the needles fastened together to be immovable with respect to each other needle.

In another embodiment, a grip device of a tattooing apparatus includes a grip body having a length and an outer diameter, the length approximately perpendicular to the outer diameter, the grip body defining a cavity extending through the entire length, the grip body defining a hole extending across the outer diameter.

In another embodiment, a pivot pin for a tattooing apparatus includes: a first end having a first rotation element; a second end opposite the first end, the second end having a second rotation element; a middle portion between the first end and the second end; a rotational axis between the first rotation element and the second rotation element; a length between the first end and the second end, the length being parallel with the rotational axis; a hole extending entirely through the pivot pin, the hole being transverse to the rotational axis; and a slot extending entirely through the middle portion from the first end to the hole.

BRIEF DESCRIPTION OF THE DRAWINGS

FIG. 8 shows a needle bar assembled through a needle bar hole of a pivot pin, according to an embodiment of the invention.

DETAILED DESCRIPTION

Figure 1:
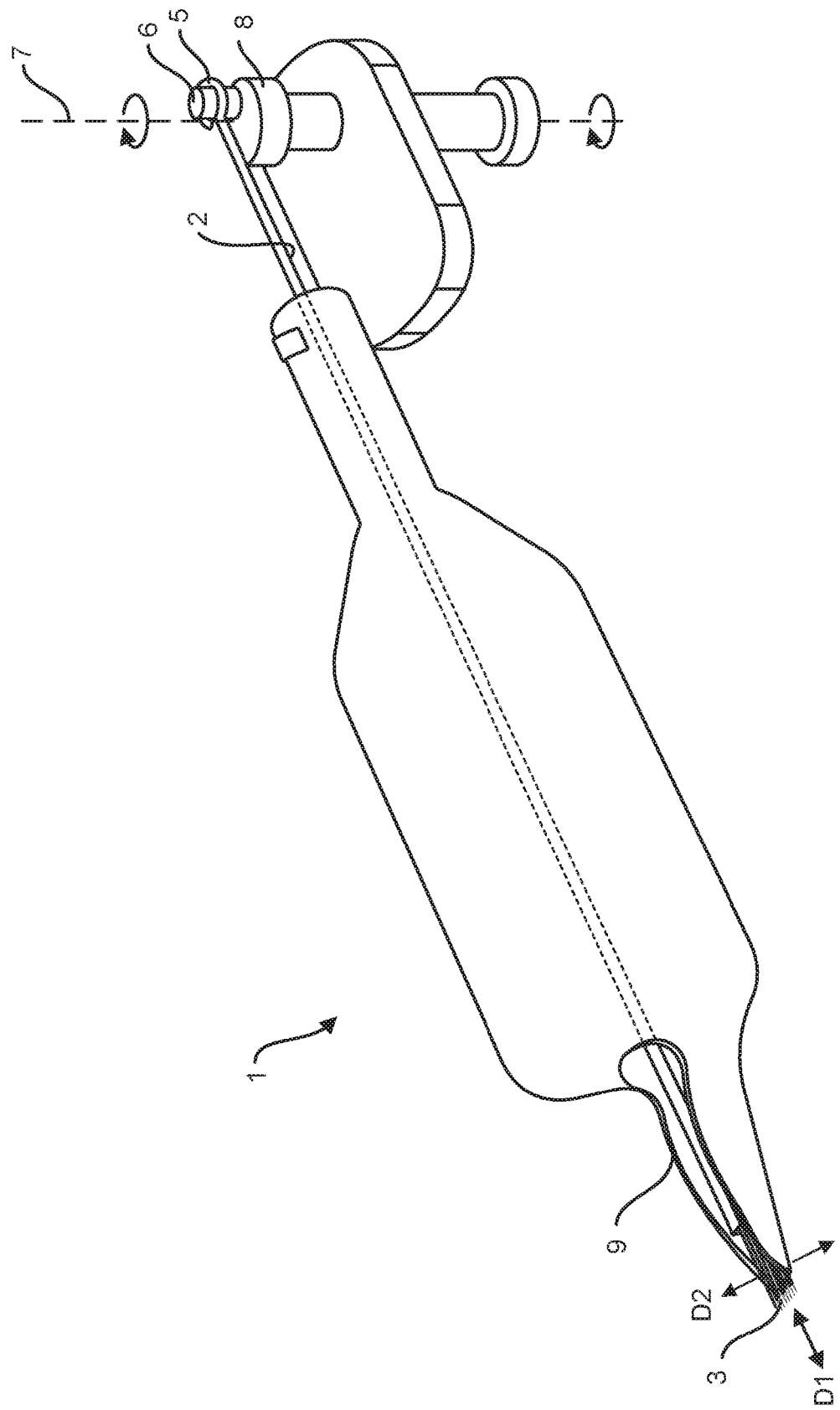
FIG. 1 shows a conventional rotary tattooing apparatus.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings, and it is to be understood that other embodiments may be utilized and that changes may be made without departing from the scope of the present teachings. The following description is, therefore, merely exemplary.

The terminology used herein is for the purpose of describing particular example embodiments only and is not intended to be limiting. As used herein, the singular forms "a", "an", and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terms "axial" and/or "axially" refer to the relative position/direction of objects along a specified axis. As further used herein, the terms "radial" and/or "radially" refer to the relative position/direction of objects along the specified axis substantially perpendicular to the specified axis. Additionally, the terms "circumferential" and/or "circumferentially" refer to the relative position/direction of objects along a circumference surrounding the specified axis.

The term "elastic deformation" is understood to be a reversible change in the dimensions of a material, in which the material has a first set of dimensions when no forces are applied to it, the material transitions to a second set of dimensions when forces are applied to it, and the material transitions back to its original set of dimensions when the forces are no longer applied. Such deformation includes but is not limited to changes in spatial dimensions and combinations thereof (e.g., changes in volume, cross-sectional profile, and diameter), and can result from forces including, but not limited to, forces of compression and/or stretching under tension.

The term "approximately", when used to qualify a specific value, is intended to convey that the actual value can be within any range equal to or smaller than 10% greater than or 10% less than the specified value. For example, "two planes approximately perpendicular to each other" would mean that the two planes could be positioned with respect to each other at an angle within any range of values between 80 degrees and 110 degrees.

Figure 2:
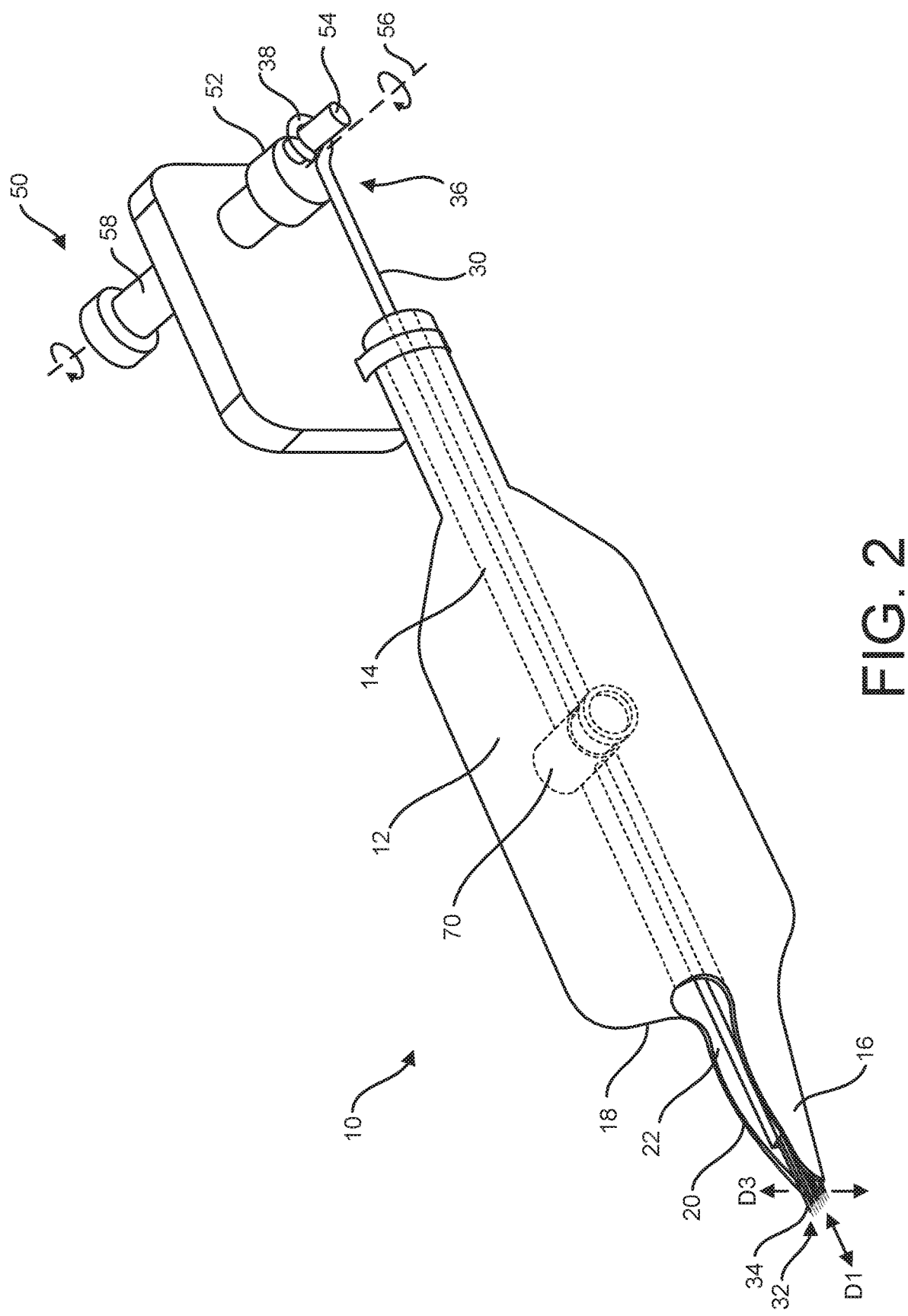
FIG. 2. is a perspective view of a tattooing apparatus transparently showing a grip body, according to an embodiment of the invention.
Figure 3:
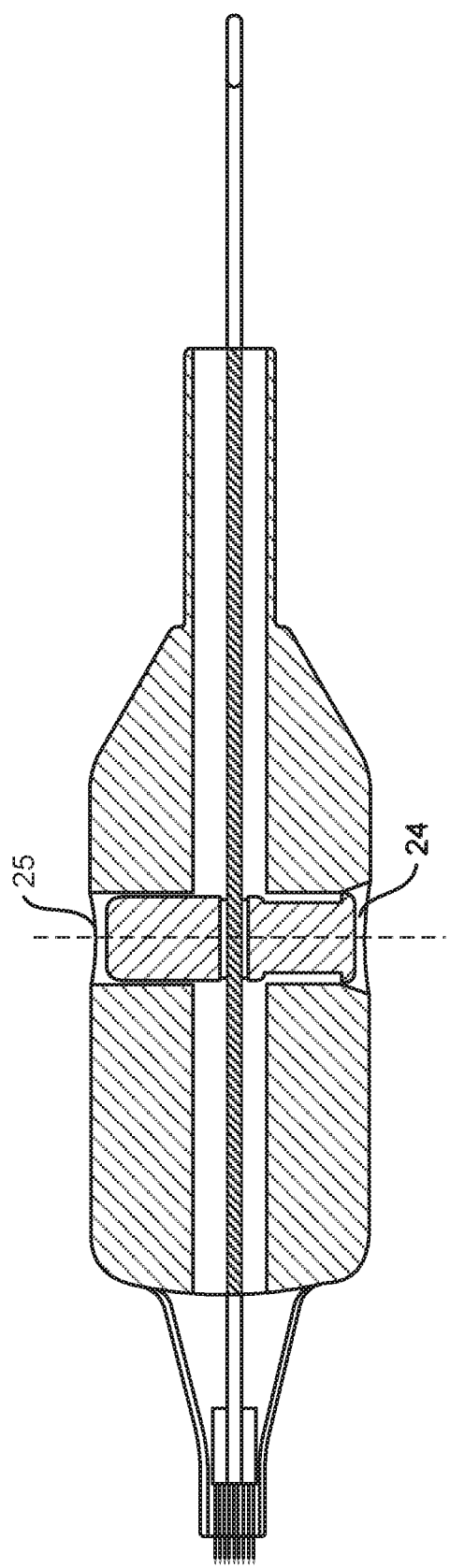
FIG. 3 is a top view of portions of the tattooing apparatus of FIG. 2.

FIG. 2 is a perspective view of a tattooing apparatus 10 according to an embodiment of the invention. The tattooing apparatus 10 includes a grip body 12, which is shown as transparent to see within a cavity 14 extending through the grip body 12. FIG. 3 shows a top view of the embodiment of FIG. 2. The grip body 12 shown is generally cylindrically shaped, though the outer shape can have any desired shape. The grip body 12 can be used as a hand grip to draw a tattoo in a person's skin, and a desired shape of the grip body 12 can be one that promotes a user's hand comfort and ease of manipulation. The smooth, cylindrical shape of the grip body 12 in the embodiment of FIG. 2 and FIG. 3 facilitates easy and comfortable rotation of the grip body 12 in a user's hand.

Still referring to the embodiment of FIGS. 2 and 3, the cavity 14 extends entirely through the grip body 12 such that a needle bar 30 can also extend entirely through the grip body 12 within the cavity 14. An ink reservoir 16, commonly called a "tube tip", extends from the grip body 12 at a needle end 18 of the grip body 12. This ink reservoir 16 can be a separate part fastened to the cavity 12 or can be integrally formed with the grip body 12. The ink reservoir 16 can include one or more reservoir walls 20 extending from the needle end 18 to define a channel 22 continuing from the cavity 14. The ink reservoir 16 (or a portion of the ink reservoir 16) can be dipped into tattoo ink, or tattoo ink can be otherwise put in the channel 22. Capillary action of the tattoo ink with surfaces of the reservoir wall(s) 20 defining the channel 22 can facilitate retention of the tattoo ink in the channel 22. At least a portion of a "top" side of the channel 22 can be left open with no reservoir wall 20 to facilitate loading ink.

Figure 4:
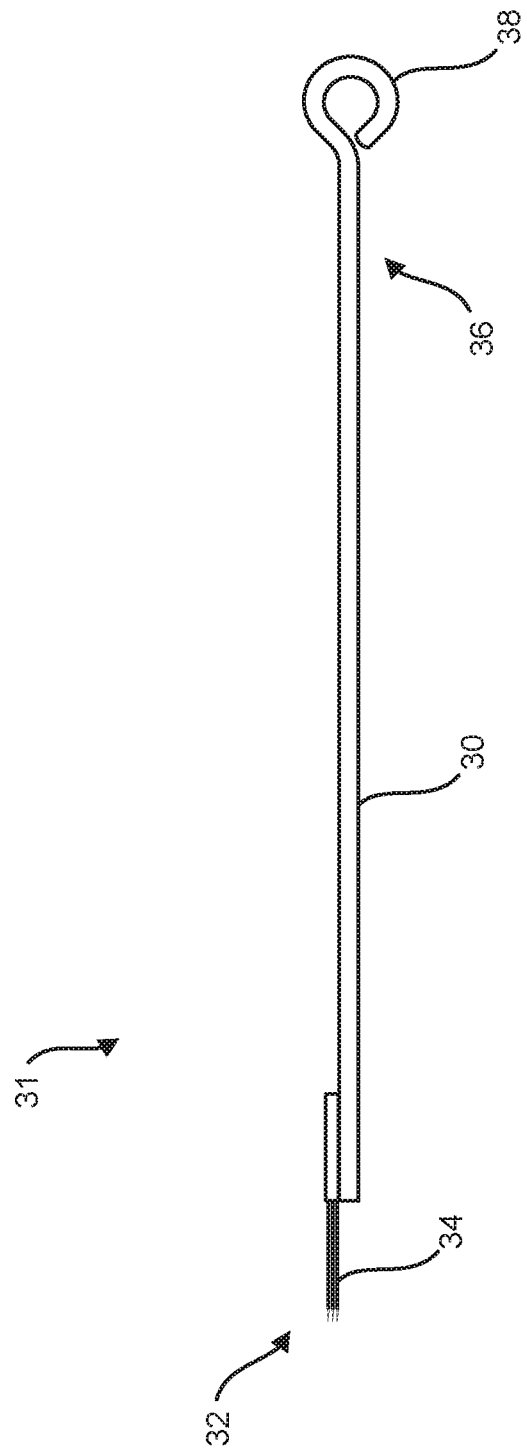
FIG. 4 is a shows a needle bar assembly according to an embodiment of the invention.
Figure 5:
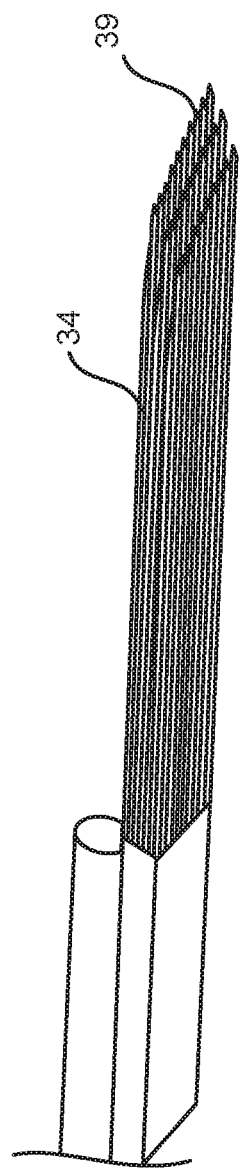
FIG. 5 is a perspective view of a group of needles, according to an embodiment of the invention.

As seen in FIGS. 2 and 3, and also FIG. 4, which shows an exemplary needle bar assembly 31, the needle bar 30 has a first end 32, to which a group of needles 34 can be coupled, and a second end 36, to which a motor attachment element 38 can be coupled. The needles 34 can be coupled to the needle bar 30 by any now-known or future-developed means to make the needles 34 immovable with respect to each other, such as, for example, soldering. The needles 34 can be positioned in any desired pattern, such as a row, as shown in FIG. 2. In some embodiments, such as the embodiment shown in FIG. 5, the needles 34 can be grouped in three rows, sometimes with at least three needles 34 in each row. Space between each adjacent row can be filled with ink to facilitate delivery of more ink. Further, the tips 39 of the needles 34 can be flattened rather than rounded, to provide more support for the ink against the effect of gravity, and to deliver more ink under the skin. A flattened edge of the flattened tip 39 can be approximately perpendicular to the first plane defined by the loop 38. As noted further below, the tattooing apparatus 10 opens a piercing wider than conventional tattooing apparatuses, enabling delivery of the larger quantity of ink this grouping of needles 34 can hold. It should be noted that while a group of needles 34 is described herein, a single needle 34 can also be used.

Referring to FIG. 2 and FIG. 3, when positioned in the cavity 14 through the grip body 12, the first end 32 of the needle bar 30 is positioned in the channel 22, such that reciprocating motion of the needle bar 30 moves the needles 34, and some ink if present in the channel 22, beyond the channel 22 to pierce a person's skin, and then to retract into the channel 22 where the needles 34 can be coated with more tattoo ink. The reservoir walls 20 can limit undesirable motion of the needles 34.

Referring to FIG. 2, at the second end 36 of the needle bar 30, the motor attachment element 38 can be coupled with a motor assembly 50. In the embodiment of FIG. 2, the motor assembly 50 includes an offset cam rotary motor assembly. A cam 52 has a driver element 54, which is a post in the embodiment of FIG. 2. The driver element 54 is offset from a rotational axis 56 of the cam 52, such that as a motor 58 drives rotation of the cam 52, the driver element 54 travels circularly, revolving around the rotational axis 56 of the cam 52. The motor attachment element 38, which in this case is a loop, though other now-known or future developed attachment structures can be used, couples with the driver element 54 (e.g., by looping around the driver element 54), to also be driven circularly around the rotational axis 56 of the cam 52. It should be noted that other configurations and various types of motors can be used in order to provide a similar rotational motion of the motor attachment element 38.

The circular motion of the attachment element 38, and hence of the needle bar 30, yields the reciprocating motion of the needles 34 to pierce and retract from a person's skin. In conventional tattooing apparatuses, the circularly reciprocating motion of the driver element 54 translates into a linear motion of needles in the piercing and retracting directions because the "side" retaining walls of the ink reservoir channel restrict and translate the circular motion of the attachment element 38 into a linear motion with a small angular shift of the needles. As compared to conventional tattooing apparatuses (e.g., see FIG. 1), the motor assembly 50 and the attachment element 38 (e.g., loop) are rotated approximately 90 degrees around a direction of piercing and retracting of the needles 34. In other words, the attachment element 38 defines, or is in, a first plane, the plurality of needles 34 can include a row of needles 34 that defines, or that are in, a second plane, and the first plane is angled approximately 90 degrees relative to the second plane. FIG. 4 shows the needle bar 30 assembled with the attachment element 38 (e.g., loop), and the needles 34 in an exemplary embodiment. This configuration would be unworkable in conventional tattooing apparatuses, engendering not only a motion with a component in the piercing and retracting directions d1, but also an erratic, non-controlled motion component in secondary directions d3 perpendicular to the piercing and retracting directions d1. These secondary directions d3 would be toward and away from the "top" side of the channel 22, where there would be space for the needles to move unrestricted, unguided, and uncontrolled. In the present invention, however, a pivot pin 70 engages the needle bar 30 to control and adjust the size and precise shape of the circularly reciprocating motion, producing a precise harmonic motion component with secondary directions d3 perpendicular to the piercing and retracting directions d1 in addition to the motion component in the piercing and retracting directions d1.

Figure 6:
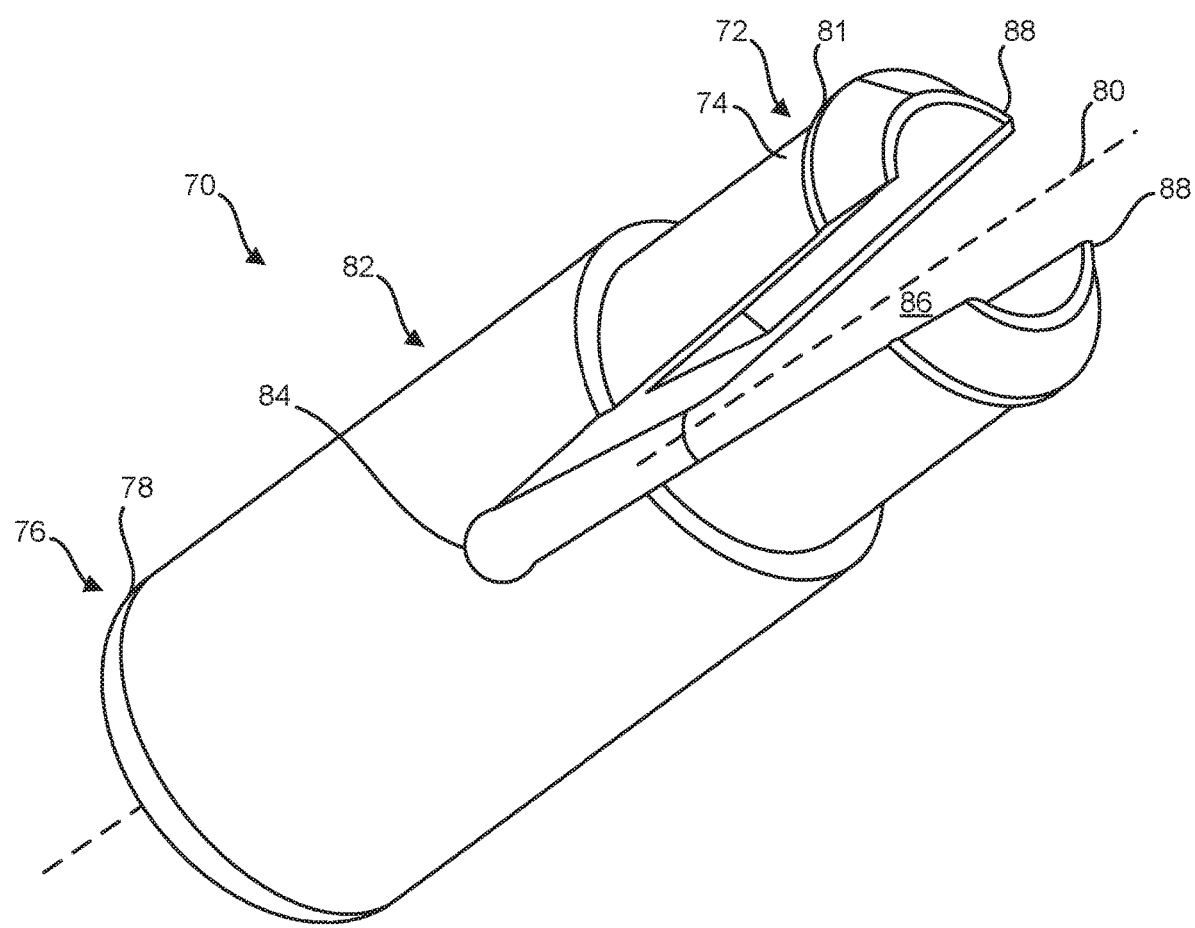
FIG. 6 is a perspective view of a pivot pin according to an embodiment of the invention.

Referring to FIG. 6, which shows a perspective view of the pivot pin 70, the pivot pin 70 includes a length extending from a first end 72 with a first rotation element 74 to a second end 76 opposite the first end 72, the second end 76 having a second rotation element 78. The first rotation element 74 and the second rotation element 78 can be any now-known or future-developed structure or device to rotate the pivot pin 70 around a rotational axis 80 of the pivot pin 70. In the depicted embodiment, the second rotation element 78 is a first smooth (e.g., low friction), cylindrically shaped outer surface having a first diameter, and the first rotation element 74 is a second smooth, cylindrically shaped outer surface having a second diameter smaller than the first diameter. A flange 81 is adjacent the first rotation element 74 at the first end 72. A middle portion 82 between the first end 72 and the second end 76 defines a needle bar hole 84 for passage of the needle bar 30 extending entirely through the pivot pin 70. The needle bar hole 84 extends transverse or perpendicular to the rotational axis 80. In some embodiments, the needle bar hole 84 extends through a diameter of the pivot pin 70. A slot 86 can extend entirely through the middle portion 82 and the first end 72, from the first end 72 to the needle bar hole 84, thereby splitting the flange 81 and creating two flexible fingers 88, which facilitates assembly of the pivot pin 70 with the grip body 12. The slot 86 can extend along the rotational axis 80 of the pivot pin 70. To increase the flexibility of the fingers 88, the fingers 88 can be hollowed adjacent the slot 86, forming a concavity in each finger 88 directly adjacent the slot 86.

Figure 7:
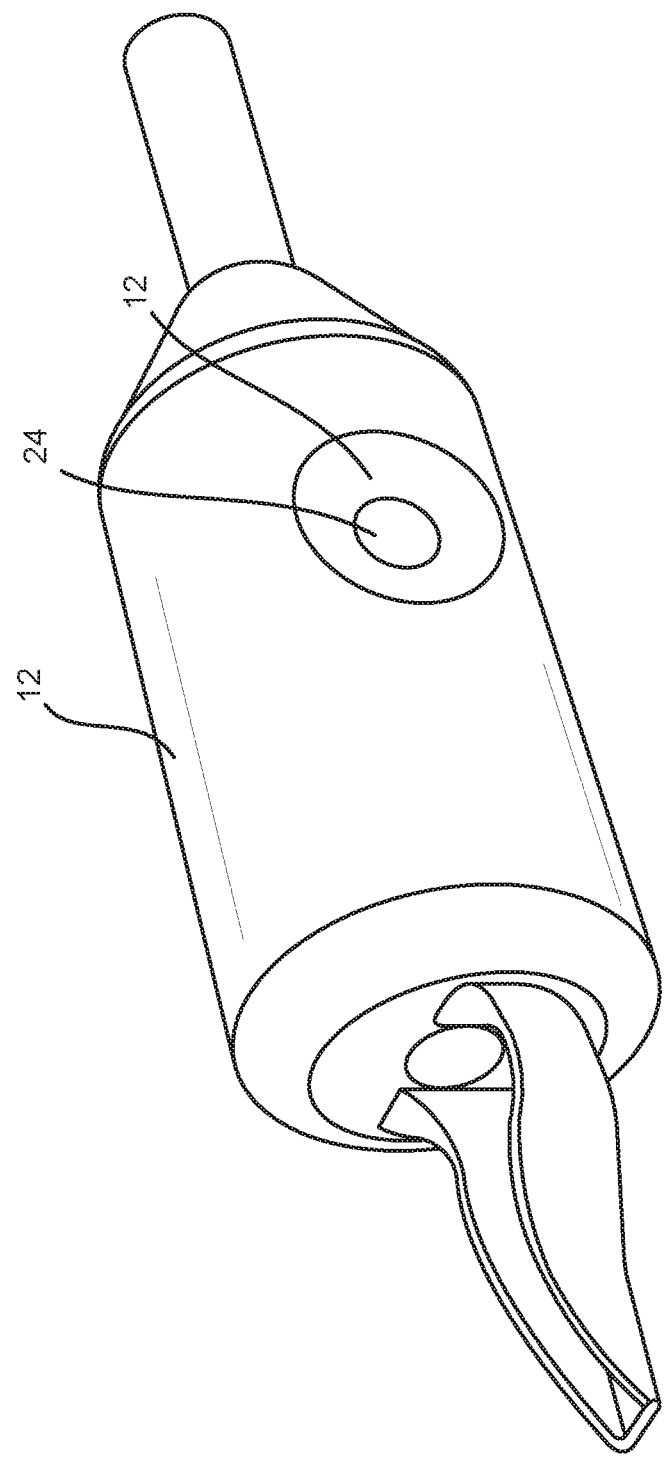
FIG. 7 shows a pivot pin mounted in a grip body, according to an embodiment of the invention.

Referring to FIGS. 2, 3, 6, and also FIG. 7, which shows the pivot pin 70 mounted in the cavity 14 with rotational axis 80 oriented perpendicular to the extension of a long axis of the cavity 14, the long axis of the cavity 14 extending entirely through the grip body 12. In other words, the pivot pin 70 can be mounted in the cavity 14 transverse with respect to the cavity 14 and the needle bar 30. The pivot pin 70 is mounted such that the pivot pin 70 can rotate around the rotational axis 80. The mounting of the pivot pin 70 can be configured in any now-known or future-developed manner such that the pivot pin 70 is held rotatably in position across the cavity 14, meaning the pivot pin 70 can rotate about the rotational axis 80, but the rotational axis 80 remains stationary and does not move along a center axis of the needle bar 30. While other manners of mounting the pivot pin 70 rotatably in the cavity 14 are conceived, in the embodiment of FIGS. 2, 3, and 6, the pivot pin 70 is held loosely on the first rotation element 74 and the second rotation element 78 by a first hole 24 and a second hole 25 in a tube wall 26 of the grip body 12, such that the pivot pin 70 cannot slide out of the first hole 24 or the second hole 25, and can rotate around the rotational axis 80. The first hole 24 can have a smaller diameter at an inner side of the tube wall 26 relative to a larger diameter at an outer side of the tube wall 26. In the depicted embodiment, the pivot pin 70 can be slid through the second hole 25 into the first hole 24, and as the pivot pin 70 slides into the first hole 14, the fingers 88 bend toward each other, allowing the flange 81 to squeeze past the smaller diameter and snap out into the larger diameter, thereby preventing the pivot pin from sliding back out the second hole 25. The needle bar 30 extending through the needle bar hole 84 also helps retain the pivot pin 70 in position.

FIG. 8 shows the needle bar 30 assembled through the needle bar hole 84. Referring to FIGS. 2, 3, and 8, the needle bar 30 can be assembled through the grip body 12, and then the pivot pin 70 can be inserted into the holes 24, 25 by straddling the needle bar 30 with the slot 86. This method of assembly enables the needle bar 30 to be preassembled with the needles 34 and the attachment element 38 before assembly with the grip body 12 and the pivot pin 70. As the attachment element 38 of the needle bar 30 is moved circularly, the needle bar 30 pushes toward the needles 34 during half the cycle and pulls toward the attachment element 38 during half the cycle. The needle bar 30 slides through the needle bar hole 84 in the piercing and retraction directions d1. Simultaneously, an up-and-down component of the circular motion of the attachment element 38 is shifted one quarter cycle from the piercing and withdrawing component, moving in secondary directions d3 perpendicular to the piercing and withdrawing directions d1, and parallel with a plane defining a direction of rotation of the pivot pin 70. The rotational axis 80 of the pivot pin 70 acts as a pivot point for the needle bar 30, such that as the attachment element 38 moves in the secondary directions d3 away from zero toward an extreme of movement of the attachment element 38 in these secondary ("up and down") directions d3, the pivot pin 70 rotates to allow the needles 34 to move in opposite secondary directions d3.

The placement of the pivot pin 70, and hence the pivot point of the needle bar 30 determines a secondary stroke range of the needles 34, wherein the secondary stroke range is the distance of movement perpendicular to the piercing and retracting component of motion of the needles 34 and parallel with the plane defining a direction of rotation of the pivot pin 70 (i.e., the range of movement in the up and down direction). Mounting the pivot pin 70 closer to the needles 34 decreases the secondary stroke range, while mounting the pivot pin 70 closer to the attachment element 38 increases the secondary stroke range.

The resulting motion of the needles 34 improves tattoo ink delivery into the skin. As the needles 34 pierce the skin, rather than pushing straight in and pulling straight out, the needles 34 push in and pull out while moving in the secondary stroke directions d3, which pulls the pierced skin opening wider, allowing a greater opportunity for greater volumes of ink and/or greater sizes of pigment particle to enter. Accordingly, a tattoo ink with pigment particles larger than pigment particles found in conventional tattoo inks can be used. Further, a needle grouping, such as the three-row grouping of FIG. 5, which is capable of holding and delivering greater volumes of ink, can also be used. Flattened needles, in addition to being able to hold more ink, are less rigid and more flexible (e.g., in the secondary directions d3) than rounded needles, allowing the skin to be pulled more gently and safely. As a result, more vibrant, longer lasting tattoos can be created.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

We claim:

1. A tattooing apparatus comprising:
a grip body defining a cavity extending therethrough in a first direction; and
a pivot pin mounted in the cavity perpendicular to the first direction, the pivot pin having an axis of rotation, the pivot pin being mounted rotatably around the axis of rotation, the pivot pin having a hole extending therethrough approximately perpendicular to the axis of the rotation of the pivot pin.

2. The tattooing apparatus of claim 1, wherein the grip body further defines a hole extending through the grip body approximately perpendicular to the first direction, the hole configured to receive the pivot pin.

3. The tattooing apparatus of claim 2, wherein the pivot pin is in the hole extending through the grip body.

4. The tattooing apparatus of claim 1, wherein the pivot pin has a first end, a second end, and a slot, the slot extending along the axis of rotation of the pivot pin through the first end to an intersection with the hole extending through the pivot pin.

5. The tattooing apparatus of claim 4, wherein the first end includes a flange split by the slot.

6. The tattooing apparatus of claim 1, further comprising a needle bar extending through the cavity of the grip body and through the hole extending through the pivot pin.

7. The tattooing apparatus of claim 6, wherein the needle bar includes a first end with a loop and a second end with a plurality of needles in a row, the loop defining a first plane, the plurality of needles in a row defining a second plane, the first plane angled approximately 90 degrees relative to the second plane.

8. A grip device of a tattooing apparatus, the grip device comprising:
a grip body having a body wall that defines a length and an outer perimeter, the body wall enclosing a cavity extending through the length, the length approximately perpendicular to a plane of the outer perimeter, the body wall having a first hole extending therethrough from the outer perimeter to the cavity, the body wall having a second hole extending therethrough from the outer perimeter to the cavity, the first hole aligned with the second hole.

9. The grip body of claim 8, further comprising an ink reservoir, the ink reservoir extending from the grip body, the ink reservoir enclosed on at least a portion of at least three sides to define a channel continuing from the cavity.

10. The grip body of claim 8, wherein the first hole extends through the body wall in a first location, the first hole having a first diameter at the outer perimeter and a second diameter at the cavity, the first diameter being larger than the second diameter.

11. A pivot pin for a tattooing apparatus, the pivot pin comprising:
a first end having a first rotation element;
a second end opposite the first end, the second end having a second rotation element;
a middle portion between the first end and the second end;
a rotational axis between the first rotation element and the second rotation element;
a length between the first end and the second end, the length being parallel with the rotational axis;
a hole extending entirely through the pivot pin, the hole being transverse to the rotational axis; and
a slot extending entirely through the middle portion from the first end to the hole.

12. The pivot pin of claim 11, wherein the first end includes a flange split by the slot.

13. The pivot pin of claim 11, wherein the first rotation element includes a circumference configured to rotate within a hole through a wall of a tattoo grip device.

* * * * *